(12) United States Patent
Kroll-Orywahl et al.

(10) Patent No.: US 11,278,434 B2
(45) Date of Patent: Mar. 22, 2022

(54) ORTHOPEDIC JOINT DEVICE

(71) Applicant: Ottobock SE & Co. KGaA, Duderstadt (DE)

(72) Inventors: Olaf Kroll-Orywahl, Northeim (DE); André Müller, Duderstadt (DE); Gordon Siewert, Göttingen (DE)

(73) Assignee: OTTOBOCK SE & CO. KGAA ( * ) Notice: Subject to any disclaimer, the term of this patent is extended or adjusted under 35 U.S.C. 154(b) by 4 days.

(21) Appl. No.: 16/488,509

(22) PCT Filed: Jun. 6, 2018

(86) PCT No.: PCT/EP2018/064905
§ 371 (c)(1),
(2) Date: Aug. 23, 2019

(87) PCT Pub. No.: WO2018/224552
PCT Pub. Date: Dec. 13, 2018

(65) Prior Publication Data
US 2020/0038204 A1  Feb. 6, 2020

(30) Foreign Application Priority Data

Jun. 6, 2017  (DE) .................... 10 2017 112 457.8
Jul. 7, 2017  (DE) .................... 10 2017 115 267.9

(51) Int. Cl.
A61F 2/66 (2006.01)
A61F 2/70 (2006.01)
(Continued)

(52) U.S. Cl.
CPC ............. A61F 2/6607 (2013.01); A61F 2/70 (2013.01); A61F 5/01 (2013.01); A61F 5/0102 (2013.01);
(Continued)

(58) Field of Classification Search
CPC ........ A61F 2/6607; A61F 5/0127; A61F 5/01; A61F 5/0102; A61F 2/70; A61F 5/0111;
(Continued)

(56) References Cited

U.S. PATENT DOCUMENTS 2,267,848 A * 12/1941 Taylor ................... A61F 5/0102
602/16
8,696,764 B2  4/2014 Hansen et al.
(Continued)

FOREIGN PATENT DOCUMENTS

CN    101912320 A    12/2010
CN    102202613 A    9/2011
(Continued)

Primary Examiner — Yashita Sharma
Assistant Examiner — Melissa A Hoban
(74) Attorney, Agent, or Firm — Holland & Hart LLP

(57) ABSTRACT

An orthopedic joint device having a lower leg part, a foot part that is arranged on the lower leg part about a swivel axis such that it can be swivelled, at least a first energy store, and a coupling element. The coupling element can be brought into a coupling position, in which a swivelling of the foot part relative to the lower leg part about the swivel axis in a plantar flexion direction leads to an increase in the amount of energy stored in the first energy store, and a de-coupling position. The orthopedic joint device also has at least one release element, which can be brought into a release position and a locked position. The energy stored in the first energy store can be released by bringing the release element into the release position.

18 Claims, 16 Drawing Sheets

(51) Int. Cl.
  *A61F 5/01* (2006.01)
  *A61F 2/68* (2006.01)
  *A61F 2/76* (2006.01)
  *A61F 5/00* (2006.01)
  *A61F 2/74* (2006.01)

(52) U.S. Cl.
  CPC .............. *A61F 5/0127* (2013.01); *A61F 2/74* (2021.08); *A61F 2/748* (2021.08); *A61F 5/0111* (2013.01); *A61F 5/0113* (2013.01); *A61F 2002/6854* (2013.01); *A61F 2002/701* (2013.01); *A61F 2002/764* (2013.01); *A61F 2002/7625* (2013.01); *A61F 2002/7635* (2013.01); *A61F 2005/002* (2013.01); *A61F 2005/0188* (2013.01)

(58) Field of Classification Search
  CPC .............. A61F 5/0113; A61F 2005/002; A61F 2005/0188; A61F 2002/6854; A61F 2002/701; A61F 2002/745; A61F 2002/747; A61F 2002/748; A61F 2002/7625; A61F 2002/7635; A61F 2002/764; A61F 2002/5006; A61F 2002/7645; A61F 2002/74
  See application file for complete search history.

(56) References Cited

U.S. PATENT DOCUMENTS

| | | |
|---|---|---|
| 8,920,517 B2 | 12/2014 | Smith et al. |
| 9,289,316 B2 | 3/2016 | Ward et al. |
| 9,682,005 B2* | 6/2017 | Herr .................. A63B 21/0004 |
| 2004/0064195 A1 | 4/2004 | Herr |
| 2006/0069448 A1 | 3/2006 | Yasui |
| 2006/0206043 A1* | 9/2006 | Yakimovich .......... A61F 5/0125 602/16 |
| 2007/0162152 A1* | 7/2007 | Herr ..................... B62D 57/032 623/24 |
| 2007/0270976 A1* | 11/2007 | DeHarde .............. A61F 5/0127 623/27 |
| 2010/0185301 A1 | 7/2010 | Hansen et al. |
| 2011/0257764 A1* | 10/2011 | Herr ........................ A61F 2/68 623/24 |
| 2013/0006386 A1* | 1/2013 | Hansen ................. A61F 2/6607 623/24 |
| 2013/0046218 A1 | 2/2013 | Wiggin et al. |
| 2014/0330393 A1* | 11/2014 | Ward ....................... A61F 2/66 623/24 |
| 2015/0025653 A1 | 1/2015 | Jung et al. |
| 2015/0305895 A1 | 10/2015 | Boiten et al. |
| 2016/0158031 A1 | 6/2016 | Ward et al. |
| 2016/0374887 A1* | 12/2016 | Wu ........................ A61F 5/0123 623/31 |
| 2017/0105851 A1 | 4/2017 | Rouse et al. |
| 2017/0165088 A1* | 6/2017 | Lefeber ................ A61F 2/6607 |
| 2017/0367851 A1* | 12/2017 | Lincoln ................ A61F 2/6607 |
| 2019/0175364 A1* | 6/2019 | Schimmels ....... A61B 17/32002 |
| 2019/0298564 A1* | 10/2019 | Van Der Wilk ...... A61F 5/0111 |
| 2021/0106441 A1* | 4/2021 | Naseri ................. A61F 2/6607 |

FOREIGN PATENT DOCUMENTS

| | | |
|---|---|---|
| CN | 104602649 A | 5/2015 |
| CN | 104797216 A | 7/2015 |
| CN | 105517510 A | 4/2016 |
| CN | 106255477 A | 12/2016 |
| DE | 102012013141 A1 | 5/2014 |
| WO | 2008048658 A2 | 4/2008 |
| WO | 2014/005709 A2 | 1/2014 |
| WO | 2015/165981 A1 | 11/2015 |
| WO | 2016100791 A1 | 6/2016 |
| WO | 2016130150 A1 | 8/2016 |

* cited by examiner

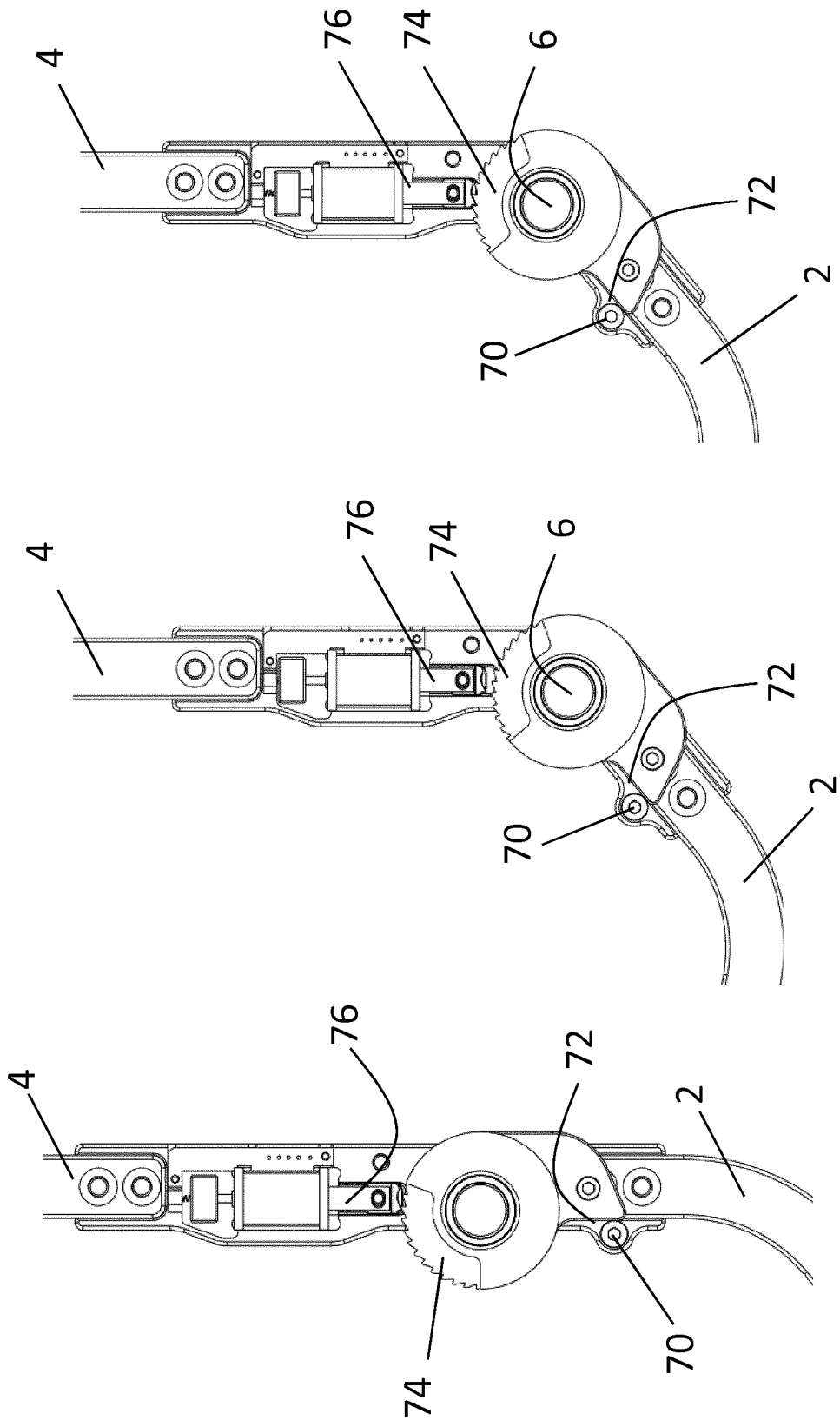

ORTHOPEDIC JOINT DEVICE

CROSS REFERENCE TO RELATED APPLICATIONS

This application is a U.S. National Entry and claims priority to PCT International Patent Application No. PCT/EP2018/064905, filed 6 Jun. 2018, and entitled "ORTHOPEDIC JOINT DEVICE", which claims priority to Germany Patent Application No. 102017115267.9 filed 7 Jul. 2017, and Germany Patent Application No. 102017112457.8 filed 6 Jun. 2017, the entire disclosures of which are incorporated herein by this reference.

TECHNICAL FIELD

The invention relates to an orthopedic joint device with a lower leg part, a foot part, which is arranged on the lower leg part about a swivel axis such that it can be swivelled, at least a first energy store and a coupling element, which can be brought into a coupling position, in which a swivelling of the foot part relative to the lower leg part about the swivel axis in a plantar flexion direction leads to an increase in the amount of energy stored in the first energy store, and into an uncoupling position.

BACKGROUND

Orthopedic joint devices have been known within the scope of the prior art for many years. They can be designed as a prosthesis or orthosis and be designed, for instance, as an ankle-foot orthosis (AFO), a knee-ankle-foot orthosis (KAFO) or a hip-knee-ankle-foot orthosis (HKAFO). In particular, the orthopedic joint device may be a drop foot orthosis. These are used in particular by patients with a weak dorsiflexion of the foot, which may develop as a result of a neural disease, such as multiple sclerosis, or following a stroke. Specifically, a weak dorsiflexion of the foot is characterized in that a movement of the foot in the dorsal flexion direction is only possible to a limited extent or not at all. A drop foot orthosis is therefore used to specifically counteract this impairment and to produce, for example, a neutral gait pattern or reduce the risk of injury or stumbling for a patient, thereby overall contributing to an improved quality of life.

To achieve this, the provision of at least one energy store has been proven to be beneficial, wherein energy can be stored in and released from said energy store over the course of a gait cycle. The energy is used, for instance, to apply a supporting force to the foot part, said force supporting the wearer when carrying out a plantar flexion or dorsal flexion.

A plantar flexion movement should be understood to mean a bending of the foot about the ankle joint axis towards the sole of the foot. The angle between the lower leg and the foot in the sagittal plane thus increases during the course of a plantar flexion movement. A dorsal flexion movement should be understood to be the opposite movement to the plantar flexion: it correlates with a decrease of the angle between the lower leg and the foot in the sagittal plane.

A person's gait cycle can generally be divided into four phases. It progresses from the so-called controlled plantar flexion phase, which begins with a touch down of the heel on the ground, the so-called "heel strike", through to a complete placing of the foot on the ground. The largest plantar flexion for this phase, which corresponds to the largest angle between the lower leg and the foot in the sagittal plane achieved in this phase, is reached when the foot is placed fully on the on the ground for the first time.

This is followed by the controlled dorsal flexion phase. Upon reaching the maximum dorsal flexion, i.e. reaching the smallest angle between the lower leg and the foot in the sagittal plane, the controlled dorsal flexion phase moves into the propelled plantar flexion phase. This transition occurs when the heel is lifted up off the ground. The propelled plantar flexion phase finishes with the loss of contact between the foot and the ground, the so-called "toe-off" and moves into the swing phase. The swing phase concludes with the next touch down of the heel on the ground, the "heel strike".

U.S. Pat. No. 8,696,764 B2, US 2004/0064195 A1 and US 2013/0046218 A1 describe drop foot orthoses that feature an energy storage device in which energy is at least partially stored during the controlled dorsal flexion phase. This energy is used to support the propelled plantar flexion. It is therefore released in this phase.

In the propelled plantar flexion phase and after the "toe-off" in particular, the wearer of a drop foot orthosis needs the support of the orthosis, as these points in the cycle require movements of the foot relative to the lower leg that must be effected by the patient using muscular strength.

The prior art includes orthoses that store energy during a plantar flexion. This energy is released during the swing phase in order to effect a dorsal flexion movement of the foot and to raise the toes. This reduces the risk of stumbling. WO 2016/130150 A1 and U.S. Pat. No. 8,920,517 B2 describe the use of hydraulic energy stores.

With regards to this type of energy store, it is particularly disadvantageous that the energy that is to be released in the swing phase must be stored in the propelled plantar flexion phase and therefore must be generated by way of muscular strength or another energy storage device. In addition to the energy for the propelled plantar flexion, the already weak muscles of the patient must therefore also generate the energy that will be stored for release during the swing phase.

The prior art therefore proposes an additional energy store, which is configured to store energy during a dorsal flexion, such that said energy can be released during a plantar flexion movement. In this type of orthesis, the second energy store is charged during the controlled dorsal flexion phase and the energy released during the subsequent propelled plantar flexion phase. Since the first energy store is charged during the propelled plantar flexion phase, the two energy stores work at least partially "against one another".

SUMMARY

The invention thus aims to propose a more efficient orthopedic joint device that overcomes the described disadvantages of the prior art.

The invention solves the problem at hand by way of an orthopedic joint device according to the preamble in accordance with the generic term in claim 1, which is characterized by the fact that the orthopedic joint device comprises at least one release element, which can be brought into a release position and a locked position, wherein the amount of energy stored in the first energy store can be released by bringing the release element into the release position.

A release element is to be understood particularly to mean an element which prevents a release of the energy stored in the energy store when said element is in the locked position. Specifically, according to the invention, the energy stored within the first energy store can be released at a desired point during the gait cycles and released in a controlled manner, by bringing the release element into the release position.

In particular, the device according to the invention renders it possible to store energy in the first energy store during the controlled plantar flexion phase and to only release this energy again after the "toe off", for instance, upon the transition between the propelled plantar flexion phase and the swing phase. A temporary discharging and charging of the energy store can therefore be omitted, preferably completely or partially.

Unlike in orthoses and prostheses from the prior art, the invention therefore allows for the de-coupling of the at least one first energy store from the movement of the foot part relative to the lower leg, without releasing the energy contained in the first energy store at this point. The release of the energy only occurs when the release element is brought into the release position. In particular, the first energy store can be charged with energy in the controlled plantar flexion phase, for example. The energy store is then de-coupled from the movement of the foot relative to the lower leg part by bringing the coupling element into the de-coupling position. Here, the release element is preferably in the locked position, such that preferably no or at least only a small amount of energy is released. The energy is preferably stored in the first energy store during the controlled dorsal flexion and the propelled plantar flexion, and preferably not released again until the swing phase. Said energy then preferably acts in the dorsal flexion direction and ideally ensures that the foot is brought into the optimal position for the next controlled plantar flexion phase, in which the first energy store is re-charged with energy.

The coupling element is designed and arranged in such a way, for example, that it can be brought into the coupling position of the de-coupling position by swivelling the lower leg part relative to the foot part about the swivel axis. In this configuration, the coupling element is, for example, a projection or a protruding pin that is arranged on the lower leg part or the foot part and preferably connected with said lower leg part or foot part such that it is torque-proof. A driver, for instance, is situated on the respective other structural component, wherein said driver can be brought into contact with the projection or pin by swivelling the foot part and the lower leg part relative to one another.

If the projection or pin is in contact with the driver, the coupling element is in the coupling position. If the projection or pin is removed from the driver by swivelling the foot part relative to the lower leg part, the coupling element is then in the decoupling position. A swivelling in the opposite direction brings the projection or pin back into contact with the driver and the coupling element therefore back into the coupling position, without having to activate the release element to do so.

The energy stored in the first energy store preferably cannot be influenced by a swivelling of the foot part relative to the lower leg part when the coupling element is in the de-coupling position. Consequently, no energy can be released so long as the release element is not in the release position; however, as long as the coupling element is in the de-coupling position, no additional energy can be stored in the first energy store either by way of a further plantar flexion. Alternatively, the amount of energy stored in the first energy store can be further increased when the coupling element is in the coupling position and an extended plantar flexion occurs.

The orthopedic joint device preferably has an electric control system which is configured to bring the at least one release element out of the locked position and into the release position. The opposite direction is preferably also possible, such that multiple switching between the two positions is possible.

Specifically, the release of the energy stored in the at least one energy store can thus be automated and occur, for instance, depending on temporal or other parameters.

The fact that the electric control system is configured to bring the at least one release element out of the locked position and into the release position and vice-versa should be understood especially to mean that the electric control system drives at least one actuator, for instance, which then brings the release element out of the locked position and into the release position and vice-versa, especially mechanically. To this end, the electric control system features at least one electronic data processing device, preferably a microprocessor, and at least one memory. Alternatively, it may simply be ensured that access to such a memory can occur.

Preferably, the orthopedic joint device has at least one sensor, in particular a pressure, position, force, path, angle, relative angle and/or acceleration sensor, and/or a sensor that can be used to detect an amount of energy contained in the energy store. This sensor is preferably configured to record at least one measured value and to transmit it to the electric control system.

Specifically, this renders it possible, by means of the at least one sensor, to obtain information that indicates which phase of a gait cycle the wearer of the orthopedic joint device is in. To this end, the at least one sensor preferably continuously records measured values and transmits them to the electric control system. Alternatively, the at least one sensor only records measured values at certain time intervals and transmits them to the electric control system. The sensor preferably contains its own data processing device that allows it to process the recorded measured values, their derivatives or integrals; to compare these, for instance, with saved threshold values; and only to transmit the measured values, their derivatives or integrals to the electric control system when the saved threshold value is exceeded or not met.

This renders it possible, by means of at least one pressure sensor that is arranged, for example, on an underside of the foot part, preferably in the heel area, that faces towards the ground during operation of the orthosis, to detect whether the drop foot orthosis is in contact with the ground. In particular, this allows a determination to be drawn on whether the drop foot orthosis is in the swing phase of the gait cycle.

The orthopedic joint device preferably features at least two sensors, especially pressure sensors. These are preferably arranged in a heel area of the foot part, said heel area being in the heel region of the wearer when in the mounted state, and a forefoot area of the foot part, said forefoot area being in the forefoot region of the wearer when in the mounted state. The advantage of this is that it not only enables the detection of a complete loss of contact with the ground, but also the differentiation between different phases, for example by determining how the load shifts from the heel area to the forefoot area. Alternatively or additionally, it is possible to detect when ground contact remains in the forefoot area only, for instance prior to the "toe-off" in the gait cycle. The practical use of at least two pressure sensors therefore allows for a considerably more detailed representation of the gait cycle.

The orthopedic joint device comprises at least two different sensors.

The angle and/or change in angle upon swivelling the foot part about the swivel axis relative to the lower leg part can be determined by at least one particularly preferred sensor. As a result, the gait cycle can be depicted in an especially simple and detailed manner.

Such a sensor may be formed, for instance, of at least to position sensors, wherein at least one position sensor is arranged on the foot part and at least one position sensor on the lower leg part. The distance between the two sensors can be used to determine the angle between the foot part and the lower leg part, if both the position of the position sensors on the foot part and the lower leg part and the swivel axis are known.

In particular, the transmission of the measured value may be achieved via a data cable or wireless transmission, for instance via radio, WiFi or Bluetooth.

Preferably, the electric control system is configured to bring the at least one release element out of the locked position into the release position or vice-versa, depending on the at least one transmitted measure value. This prevents energy from being released at undesired points.

To support the wearer of the orthopedic joint device with the dorsal flexion that occurs during the swing phase, is it especially practical to coordinate the release of the energy from the at least one energy store with the start of the swing phase, i.e. specifically, the point at which the foot is lifted up off the ground ("toe-off").

Furthermore, the release element can be brought from the release position into the locked position at the point of maximum plantar flexion in the controlled plantar flexion phase, for instance, such that the energy stored in the at least one first energy store during the controlled plantar flexion is either not fully or partially released during the dorsal flexion phase.

It is therefore beneficial if the electric control system is configured to detect a loss of ground contact of the orthopedic joint device using the at least one transmitted measured value, and to bring the release element out of the locked position into the release position when the loss of ground contact has been detected.

It is also beneficial if the electric control system is configured only to bring the coupling element from the coupling position into the de-coupling position when the release element is in the locked position.

The amount of energy in the at least one energy store increases particularly in the controlled plantar flexion phase. Consequently, the maximum possible energy input in this phase is achieved upon reaching the maximum plantar flexion. If the at least one energy store is a spring element, it is beneficial if, upon reaching the maximum plantar flexion, the energy store is de-coupled by means of the coupling element from the movement of the foot part relative to the lower leg part, as the subsequent controlled dorsal flexion would cause the at least one energy store to discharge once again. However, the de-coupling of the spring element while the release element is in the release position would lead particularly to a partial or complete release of the energy by way of the slackening of the spring element. It is therefore practical to first of all bring the release element from the release position into the locked position and only then to bring the coupling element from the coupling position into the de-coupling position. The release element is preferably brought into the locked position as soon as all the energy stored in the energy store has been released in the swing phase, for example.

The orthopedic joint device preferably comprises at least one second energy store, which is configured in such a way that a swivelling of the foot part relative to the lower leg part about the swivel axis in a dorsal flexion direction leads to an increase in the amount of energy stored in the second energy store.

Specifically, such a second energy store is beneficial with regards to supporting the wearer of the orthosis during the propelled plantar flexion phase. This allows the at least one second energy store to absorb energy during the controlled plantar flexion phase, wherein said energy is released again, in particular in the subsequent propelled plantar flexion phase.

Furthermore, this combination in particular allows for the energy from the at least one first and the at least one second energy store to be used synergistically, since the "working against one another" from the prior art does not apply. In this way, the energy from the at least one second energy store is preferably first of all released in the propelled plantar flexion phase; following the "toe-off", the energy from the at least one first energy store is then released by bringing the release element into the release position.

The at least one first energy store and/or the at least one second energy store preferably is/are a spring element and/or a hydraulic and/or a pneumatic device.

In particular, the spring element refers to a helical spring or a torsion spring. It is also possible for energy to be stored in such a spring element by means of a hydraulic device. Furthermore, it is also possible for energy to be stored by compressing a gas using a pump or a compressor. In particular, it is also possible for several different types of first and/or second energy stores to be provided in an orthopedic joint device.

In mechanical energy stores, especially spring elements, the release element is, for example, a ratchet element or an overriding element. If a pneumatic or hydraulic energy store is used, the release element is preferably a valve that can be switched, in particular electrically or electronically. The coupling element may also be a fluid.

In a variation of the invention, the coupling element is designed as a fluid-valve combination. This renders it possible to execute a dorsal extension at a desired and freely selectable point in time.

If two rotary hydraulics are allocated to the joint device, preferably medially and laterally, it is possible to execute an alternating energy store and energy release in different directions, namely plantar flexion and dorsal extension. This enables the execution of an extended dorsal extension, without this having an adverse impact on the influence of the plantar flexion.

BRIEF DESCRIPTION OF THE DRAWINGS

In the following, examples of embodiments of the present invention will be explained by way of the attached drawings: They show FIGS. 1, 3, 5, 7 and 9—schematic diagrams of different embodiments of orthopedic joint devices, FIGS. 2, 4, 6, 8 and 10—the examples of embodiments depicted in the respective preceding figures in different movement phases, FIGS. 11 and 12—schematic depictions of the hydraulic/pneumatic systems, FIG. 13—a schematic depiction of an orthopedic joint device, FIG. 14—a schematic depiction of the flow of energy in the energy storage elements according to the example of an embodiment in FIG. 2, and FIGS. 15-20—different phases of a step in an example of an embodiment of the present invention.

DETAILED DESCRIPTION

Figure 1:
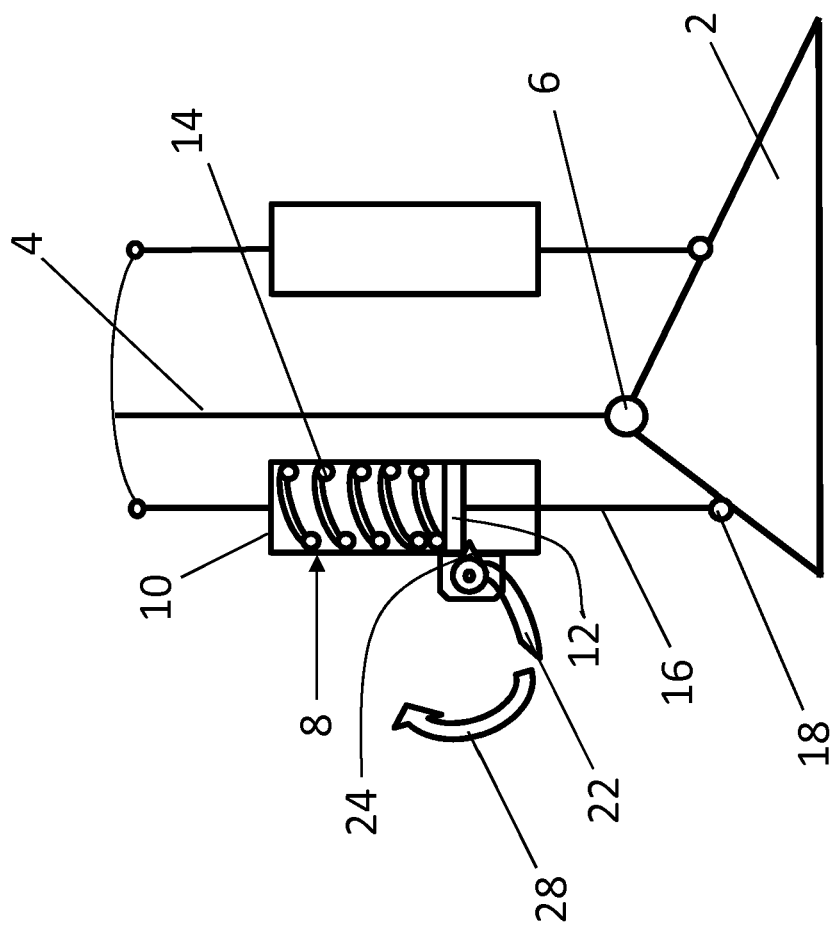

FIG. 1 shows a schematic depiction of an orthopaedic device according to a first example of an embodiment of the present invention. It has a foot part 2, which is mounted on a lower leg part 4 about a swivel axis 6 such that it can be swivelled. It also features a first energy store 8, which comprises a piston 12 that is moveably mounted in a cylinder 10 in the example of an embodiment shown, said piston being pre-loaded by a spring 14. A plunger 16 is arranged on the piston 12, said plunger being connected to the foot part 2 via a coupling element 18.

Figure 2:
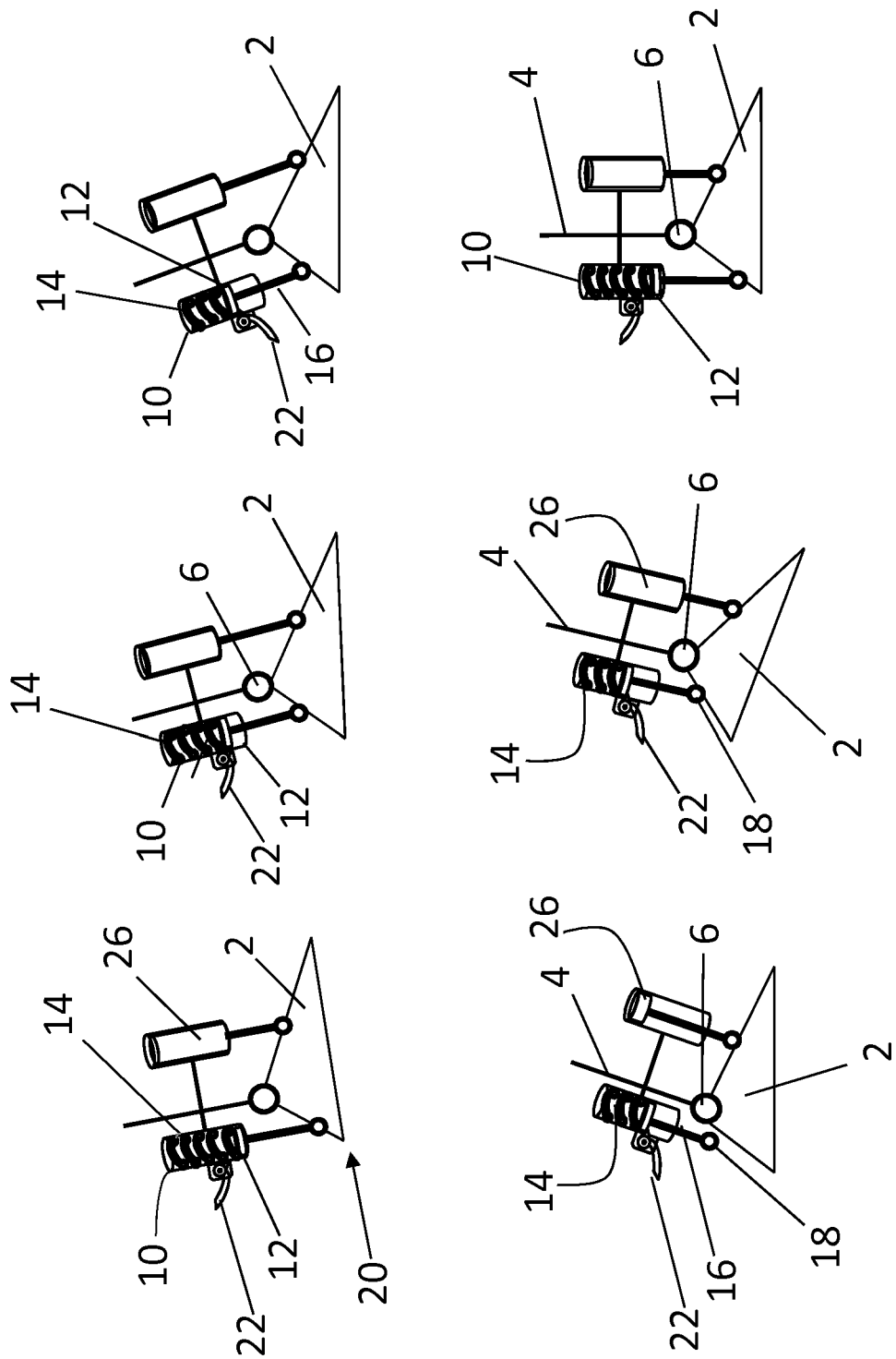

In FIG. 2, this embodiment of an orthopedic joint device is shown in different movement phases of a step. The top left-hand image shows the situation when the heel strikes the ground. The foot part 2 is blocked against the horizontal tilt and a heel 20 comes into contact with the ground when the foot touches down. The spring 14 is slackened as much as possible and the piston 12 is situated at the lower end of the cylinder 10. The image to the right depicts the situation during an unrolling of the foot, i.e. the controlled plantar flexion. In contrast to the situation shown in the left-hand image, the foot part 2 has been swivelled in the plantar flexion direction about the swivel axis 6. The piston 12 has been moved upwards in the cylinder 10, thereby compressing the spring 14 and thus increasing the energy content of this energy store. The top right-hand image shows the situation in which the foot part lies fully flat on the ground. It represents the maximum plantar flexion position in this gait. The plunger 16 has pushed the piston 12 upwards in the cylinder as far as possible, such that the spring 14 is highly compressed. In this situation, a release element 22, which was in a release position in the situations shown in the top left-hand and middle images in FIG. 2, is brought out of this release position and into the locked position. This is shown in more detail in FIG. 1. The release element features a pawl 24, which fixes the piston 12 in the cylinder 10 in the position depicted. During the subsequent controlled dorsal flexion, which is shown in the lower left-hand image in FIG. 2, the foot part 2 is swivelled in relation to the lower leg part 4 about the swivel axis 6; however, the spring 14 does not slacken. The energy stored in the energy store 14 remains intact, as the release element 22 is in the locked position. It is also clear to see that the coupling element 18 has de-coupled the plunger 18 from the foot part 2.

In the example of an embodiment shown, a second energy store 26 can be used to provide energy for an active plantar flexion movement, which is shown in the bottom-centre image in FIG. 2. The foot part 2 is swivelled towards the lower leg part 4 about the swivel axis 6 and the coupling element 18 comes back into contact with the foot part 2. In this case, the release element 22 can be brought out of the locked position and into the release position, following the arrow 28 shown in FIG. 1, such that energy can be discharged from the spring 14, wherein the piston 12 is moved downwards within the cylinder 10. This is shown in the lower right-hand image in FIG. 2. The foot part 2 is swivelled towards the lower leg part 4 about the swivel axis 6 and the forefoot area raised.

Figure 3:
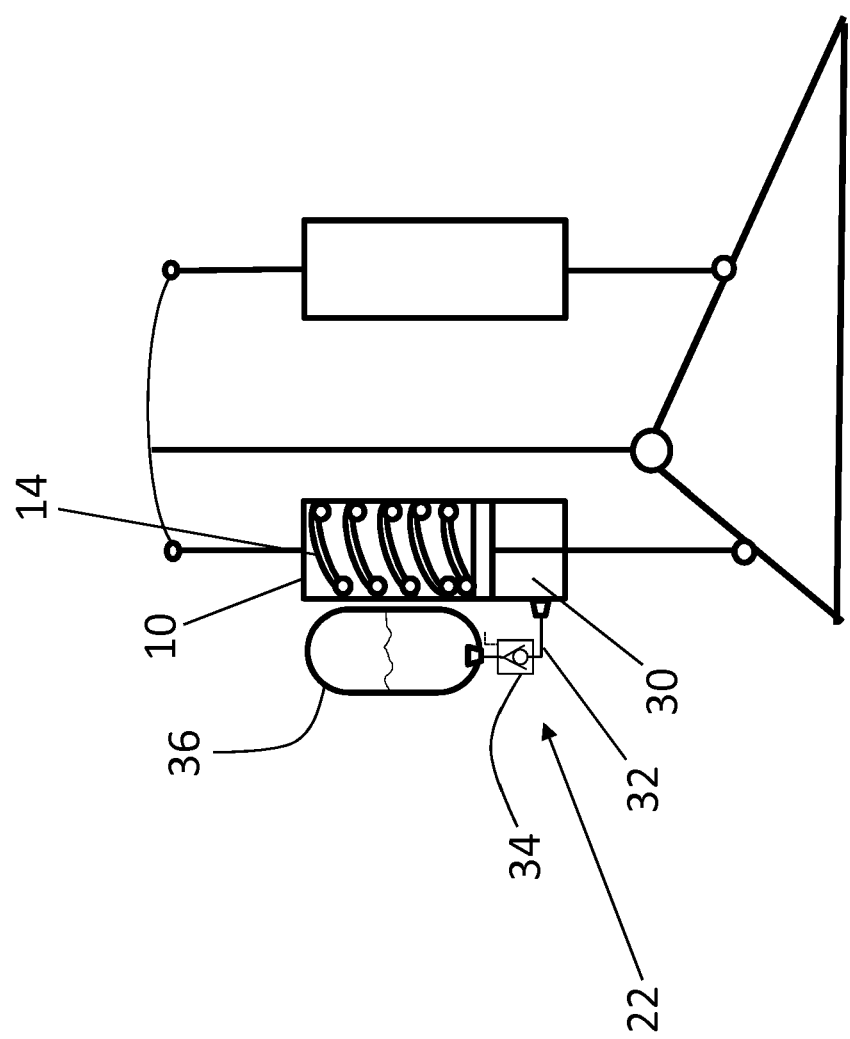

FIG. 3 shows a diagram similar to FIG. 1. The structural difference is the configuration of the release element 22. A volume 30 is situated below the spring 14 in the cylinder 10, said volume being connected to a compensation reservoir 36 via a fluid line 32, in which a switchable valve 34 is arranged.

Figure 4:
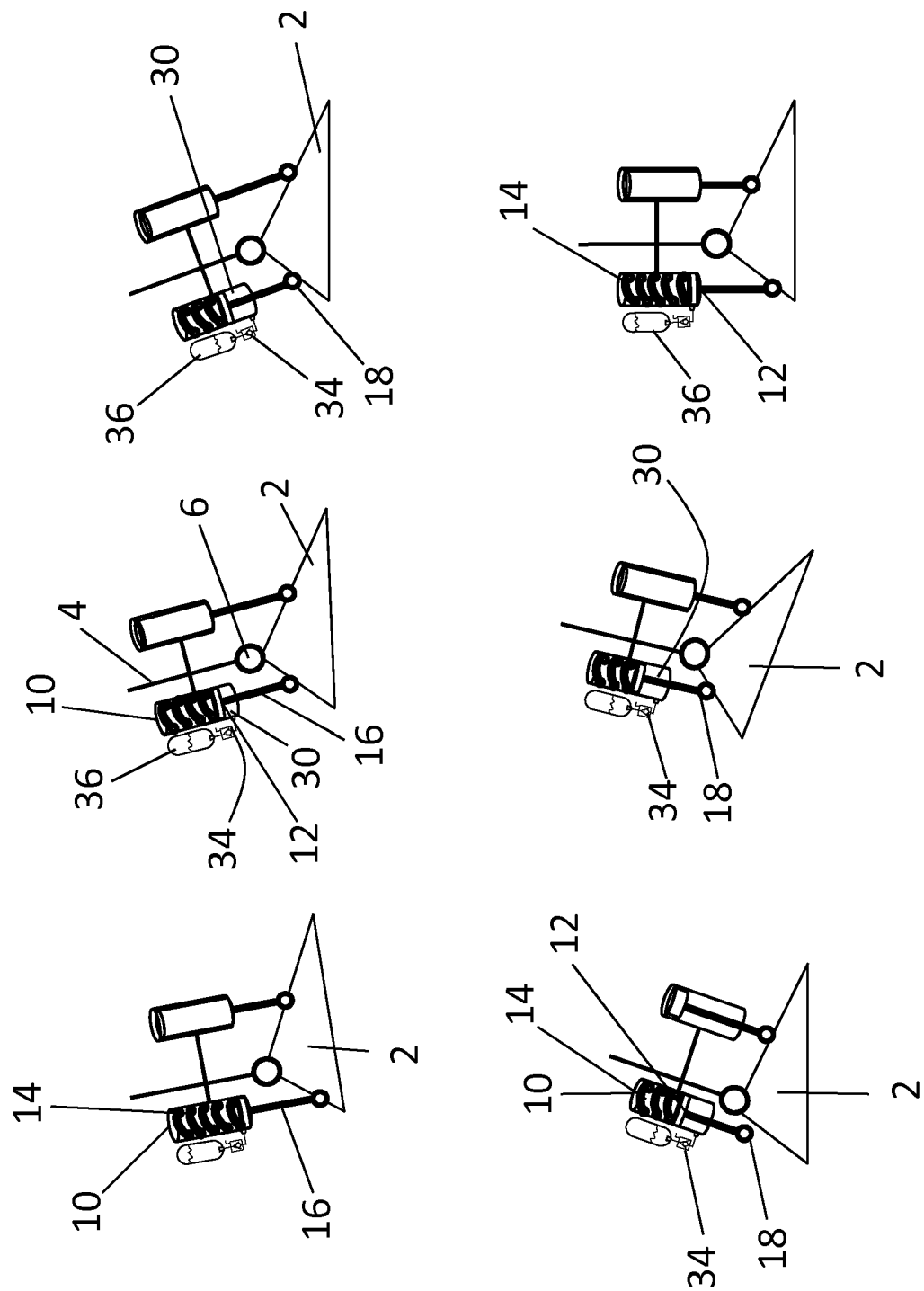

FIG. 4 depicts the configuration from FIG. 3 in the positions according to FIG. 2. When the heel of the foot part 2 strikes the ground (upper left), the plunger 16 is moved out of the cylinder 10 as far as possible, so that the spring is slackened. During the subsequent roll-over and the controlled plantar flexion, the foot part 2 is swivelled relative to the lower leg part 4 about the swivel axis 6 and, as the upper-middle image in the diagram shows, the plunger 16 is moved, along with the piston 12 arranged on it, upwards within the cylinder 10. Here, the switchable valve 34 is open, such that fluid can flow out of the compensation reservoir 36 into the volume 30. This occurs up until the maximal plantar flexion position, which is depicted in the top right-hand image in FIG. 4. In this state, the switchable valve 34 is closed, such that no fluid can flow out of the volume 30 into the compensation reservoir 36. In the example of an embodiment shown, the coupling element 18 is decoupled from the foot part 2 at the same time. The lower left-hand image in FIG. 4 shows the maximum dorsal flexion position. The coupling element 18 is not engaged with the foot part 2 and, given that the switchable valve 34 is still closed, the piston 12 has not been moved downwards in the cylinder 10, so the energy store, which is designed as a spring 14, continues to store energy. This occurs at the point shown in the middle image of the bottom row in FIG. 4. The coupling element 18 engages with the foot part 2 once again and the switchable valve 34 is opened. As a result, the spring 14 can be slackened, such that the piston 12 is moved downwards and a fluid can be directed out of the volume 30 into the compensation reservoir 36.

The switchable valve 34 can also be used as a throttle valve in such a way that the release of energy from the energy store, i.e. from the spring 14, can be executed such that it is damped. Of course, this is also possible in all other configurations in order to avoid an abrupt release of energy.

Figure 5:
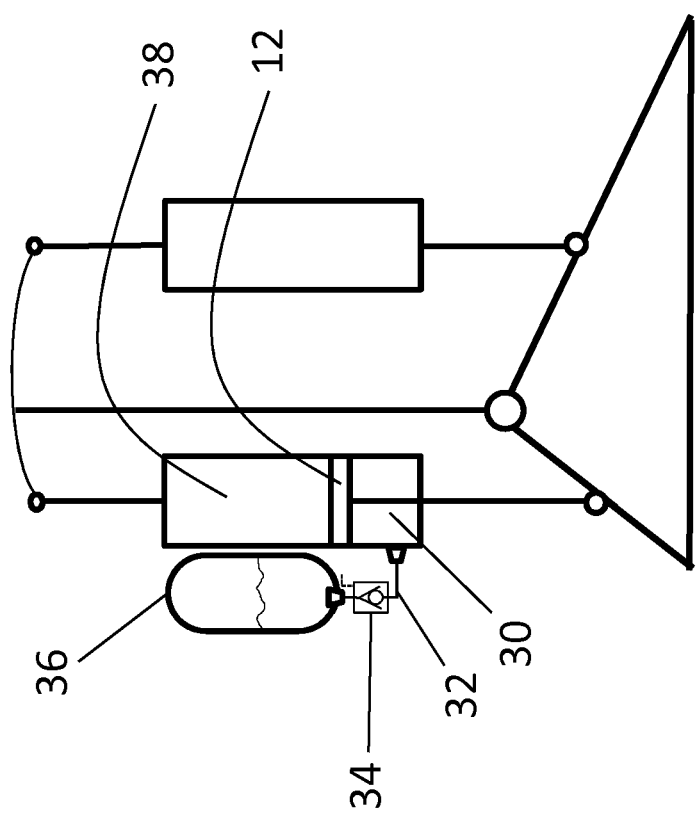

FIG. 5 shows a diagram similar to FIGS. 1 and 3. The only structural difference to the diagram in FIG. 3 lies in the form of the energy store. A pressure accumulator 38 is provided instead of the spring 14, wherein said pressure accumulator contains a compressible medium. The volume 30 that is situated below the piston 12 is again connected to the compensation reservoir 36 via the fluid line 32 and the switchable valve 34.

Figure 6:
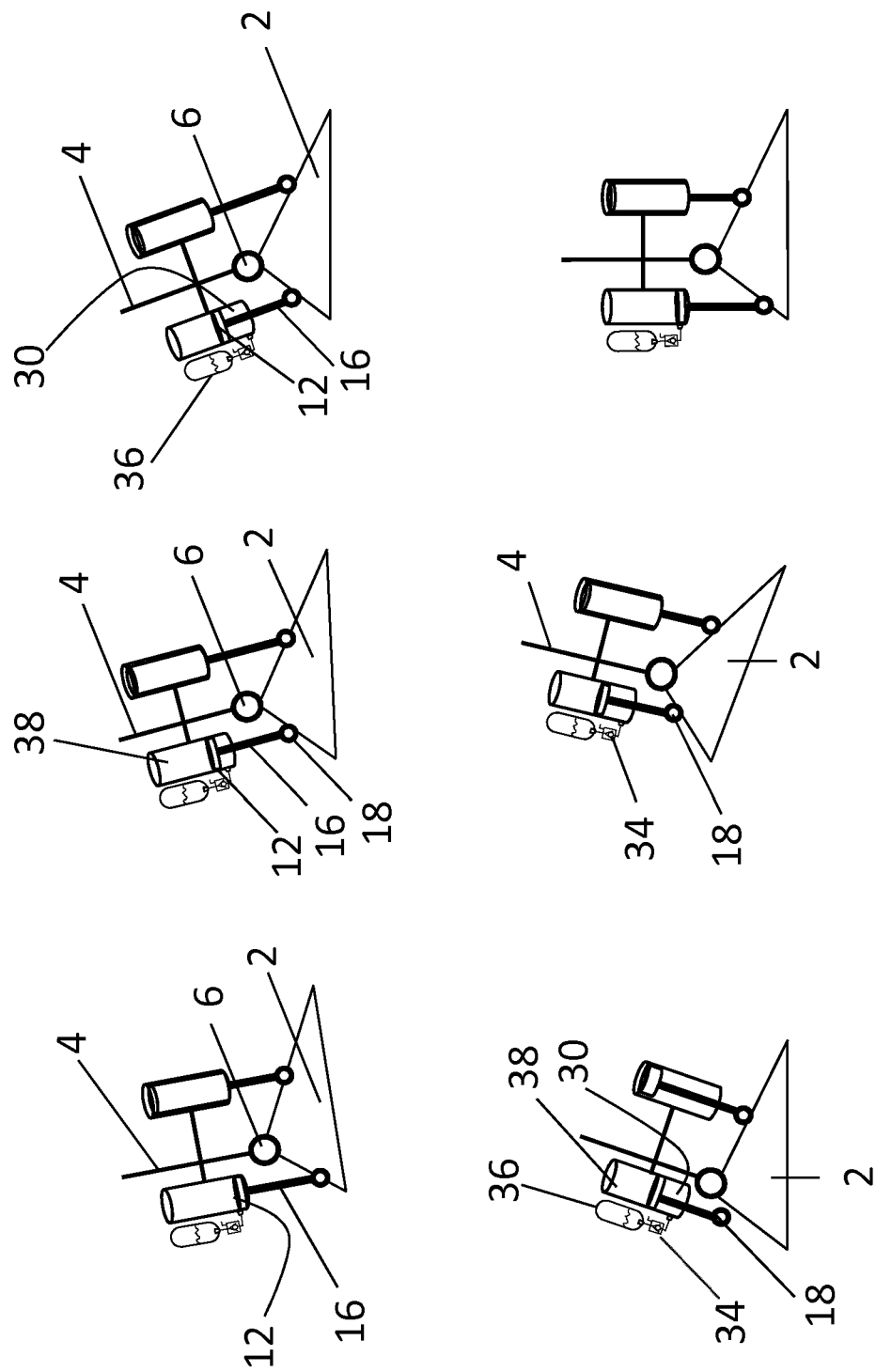

FIG. 6 shows the example of an embodiment depicted in FIG. 5 in the various movement phases. Following the heel strike (upper left), the foot part 2 is swivelled relative to the lower leg part 4 about the swivel axis 6 in a plantar flexion direction. Here, the plunger 16 and therefore also the piston 12 are moved upwards. The volume 30 is filled with fluid from the compensation reservoir 36. The pressure accumulator 38, in which the compressible medium is situated, is compressed, such that energy is stored in the form of pressure.

This is followed by the coupling element 18 being disengaged from the foot part 2 and the switchable valve 34 being closed, such that no more fluid can flow from the volume 30 into the compensation reservoir 36. As a result, the pressure from the pressure accumulator 38 cannot be reduced during the dorsal flexion shown in the bottom left-hand image in FIG. 6. It is only when the foot part 2 is once again in the depicted position relative to the lower leg part 4 during the actively propelled plantar flexion (bottom-middle in FIG. 6) that the coupling element 18 is reengaged and the switchable valve 34 opened.

Figure 7:
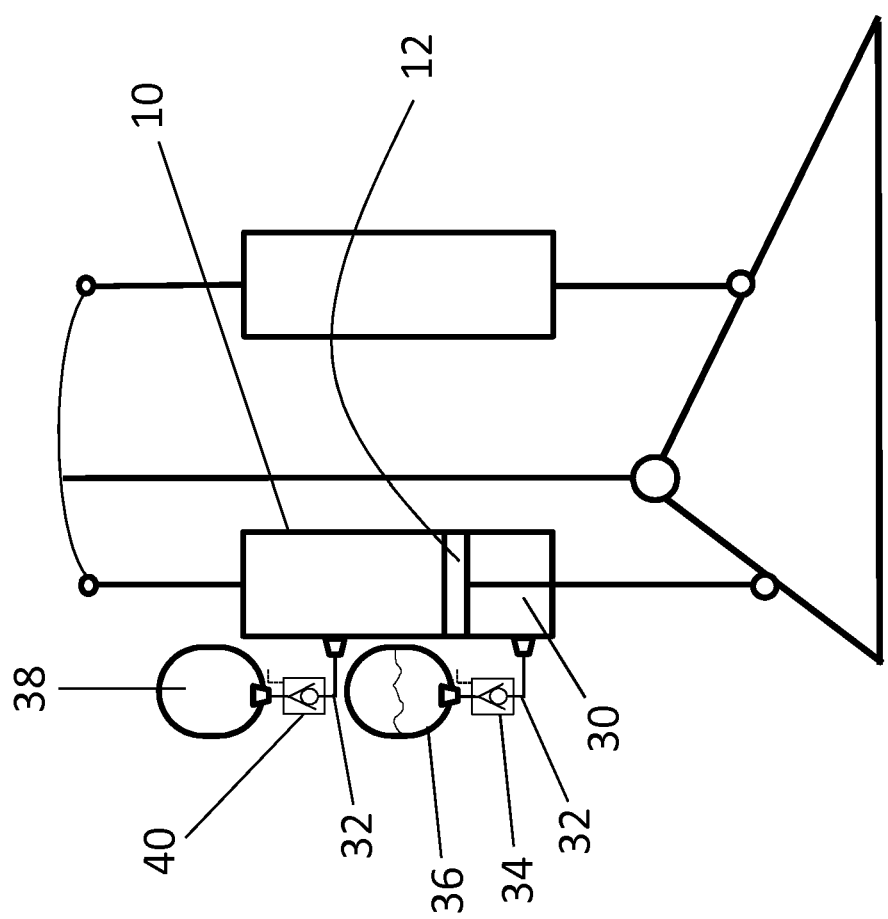
Figure 8:
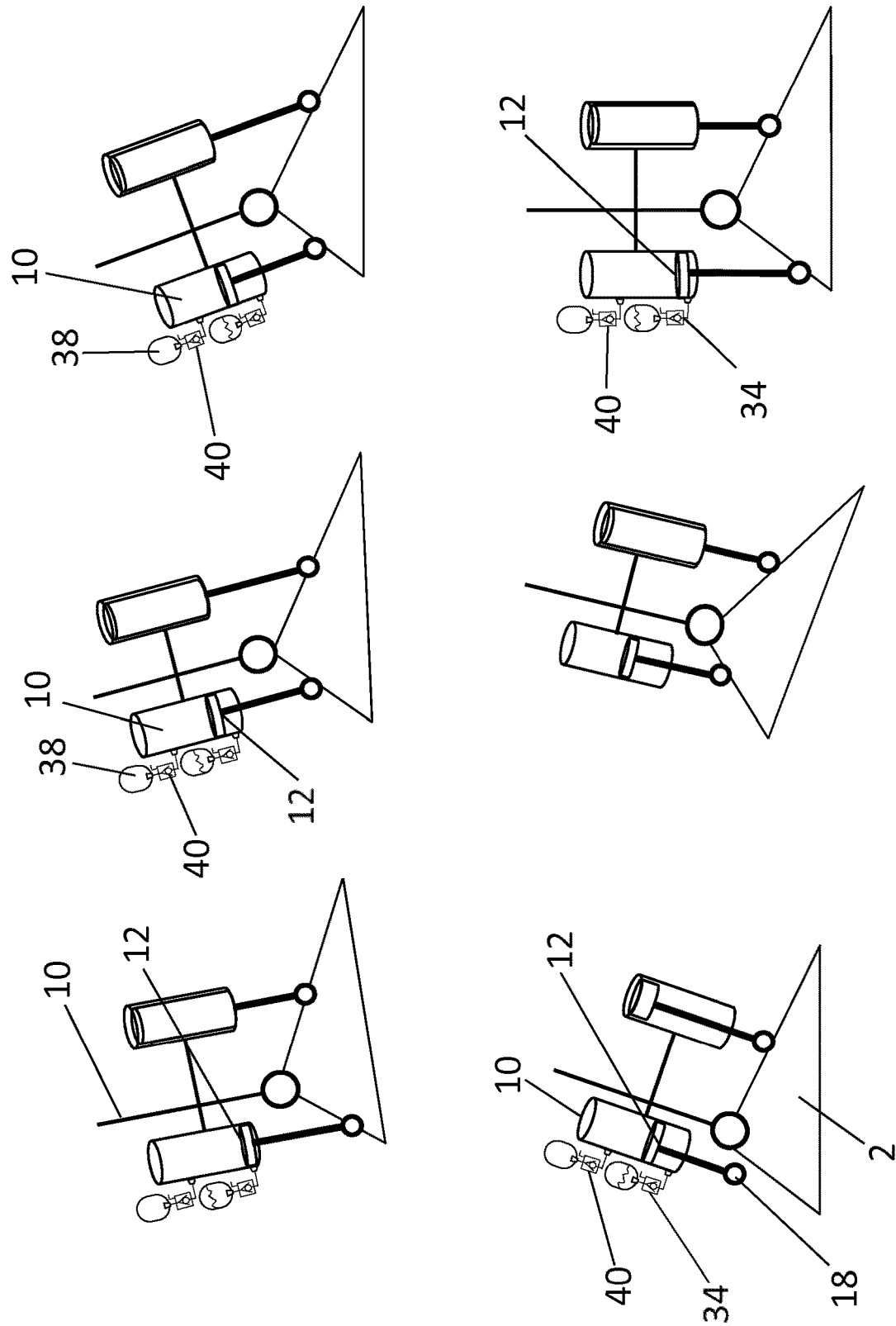

FIG. 7 shows another altered embodiment. The volume 30 below the piston 12 is connected to the compensation reservoir 36 via the fluid line 32 and the switchable valve 34. The pressure accumulator 38 is now arranged outside of the piston 10 and also connected to the piston 10 via a fluid line 32 and a second switchable valve 40. FIG. 8 shows these configurations in different movement phases. The functionality corresponds to the functionality that was explained regarding FIG. 6.

By moving the piston 12 upwards inside the cylinder 10 when the second switchable valve 40 is open, a fluid is pushed out of the cylinder 10 into the pressure accumulator 38. The bottom row in FIG. 8 depicts how the second switchable valve 40 is also closed, in the same way as the switchable valve 34, such that the piston 12 cannot be moved inside the cylinder 10. The coupling element 18 is not engaged with the foot part 2.

Only when the switchable valve 34 and the second switchable valve 40 are opened, as depicted in the lower-middle and lower right-hand image in FIG. 8, can the piston 12 be moved downwards again.

Figure 9:
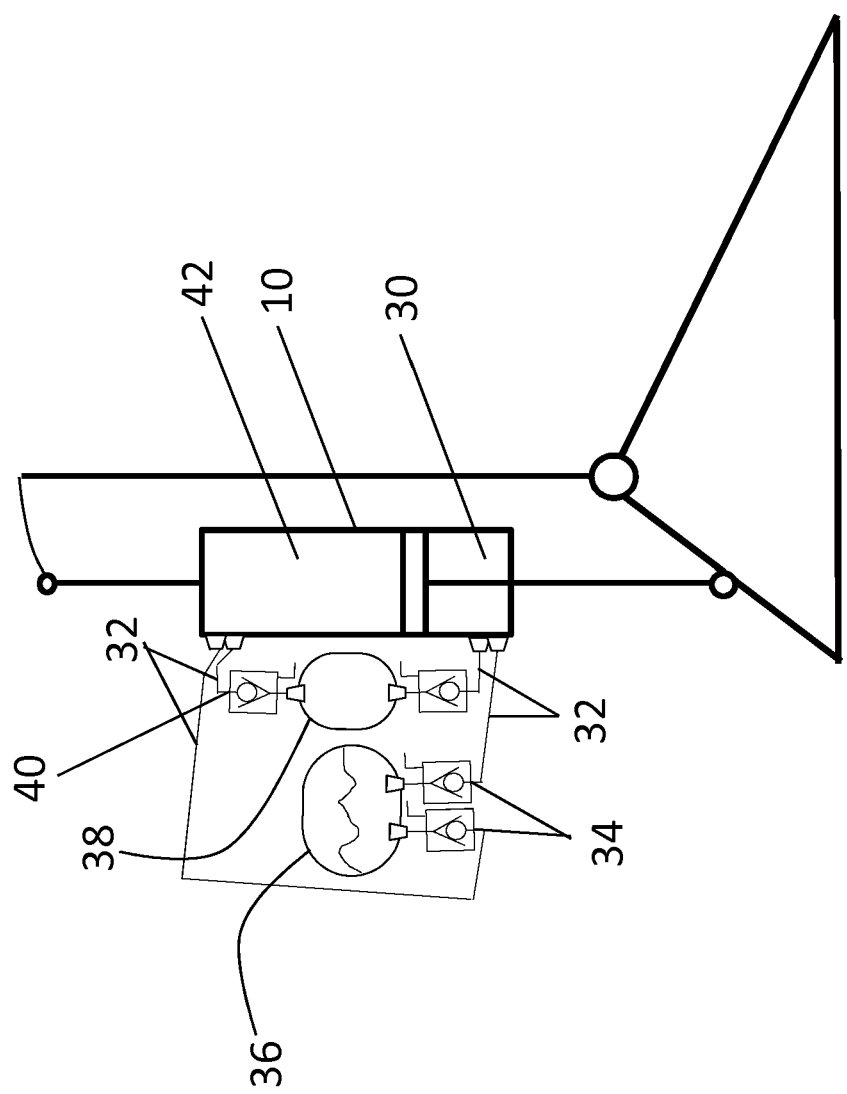

FIG. 9 shows another configuration of an orthopedic joint device. The cylinder 10 comprises two chambers, which are formed by the volume 30 and the volume 42. The joint device features the accumulator 38 and the compensation reservoir 36. Both are connected to the volume 30 and the volume 42 via a fluid line 32. A switchable valve 34 is situated in each of these fluid lines 32.

Figure 10:
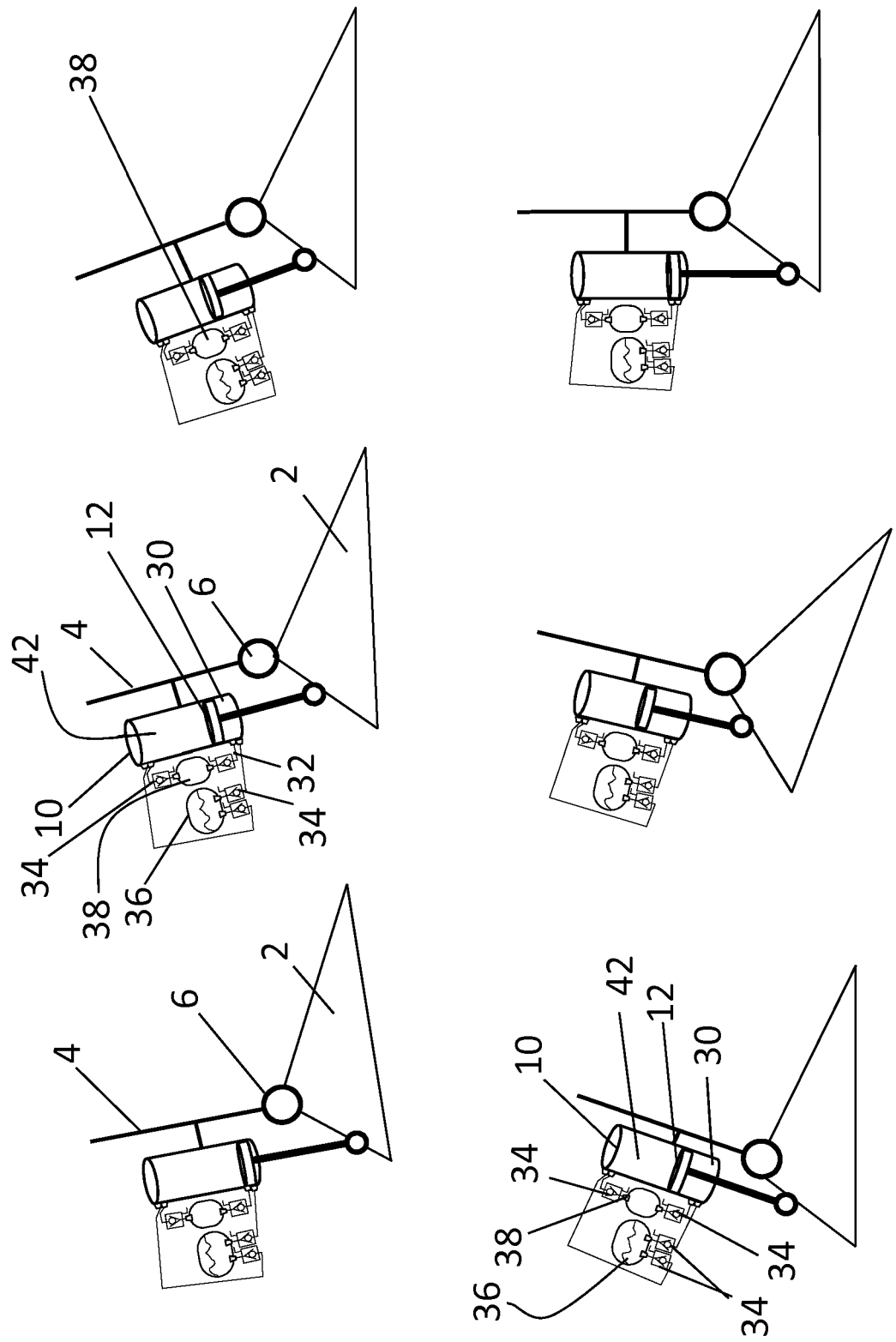

FIG. 10 depicts the configuration from FIG. 9 in the various movement phases. Following the heel strike (upper left), the foot part 2 is swivelled relative to the lower leg part 4 about the swivel axis 6. As a result, the piston 12 moves upwards in the cylinder 10. The switchable valve 34, which connects the volume 42 to the pressure accumulator 38, is also open, in the same way as the switchable valve 34 by way of which the fluid line 32 is opened, said fluid line connecting the volume 30 to the compensation reservoir 36. This movement causes a considerable increase in the pressure inside of the pressure accumulator 38. During the subsequent dorsal flexion (bottom left), the two valves 34, which connect the volumes 30, 42 to the pressure accumulator 38, are closed, while the other two valves 34, by way of which the volumes 30, 42 are connected to the compensation reservoir 36, are open. This enables the piston 12 to be moved inside the cylinder 10, without effecting a change in the pressure within the pressure accumulator 38. The valves 34 thus form part of the coupling element and/or the release element.

Figure 12:
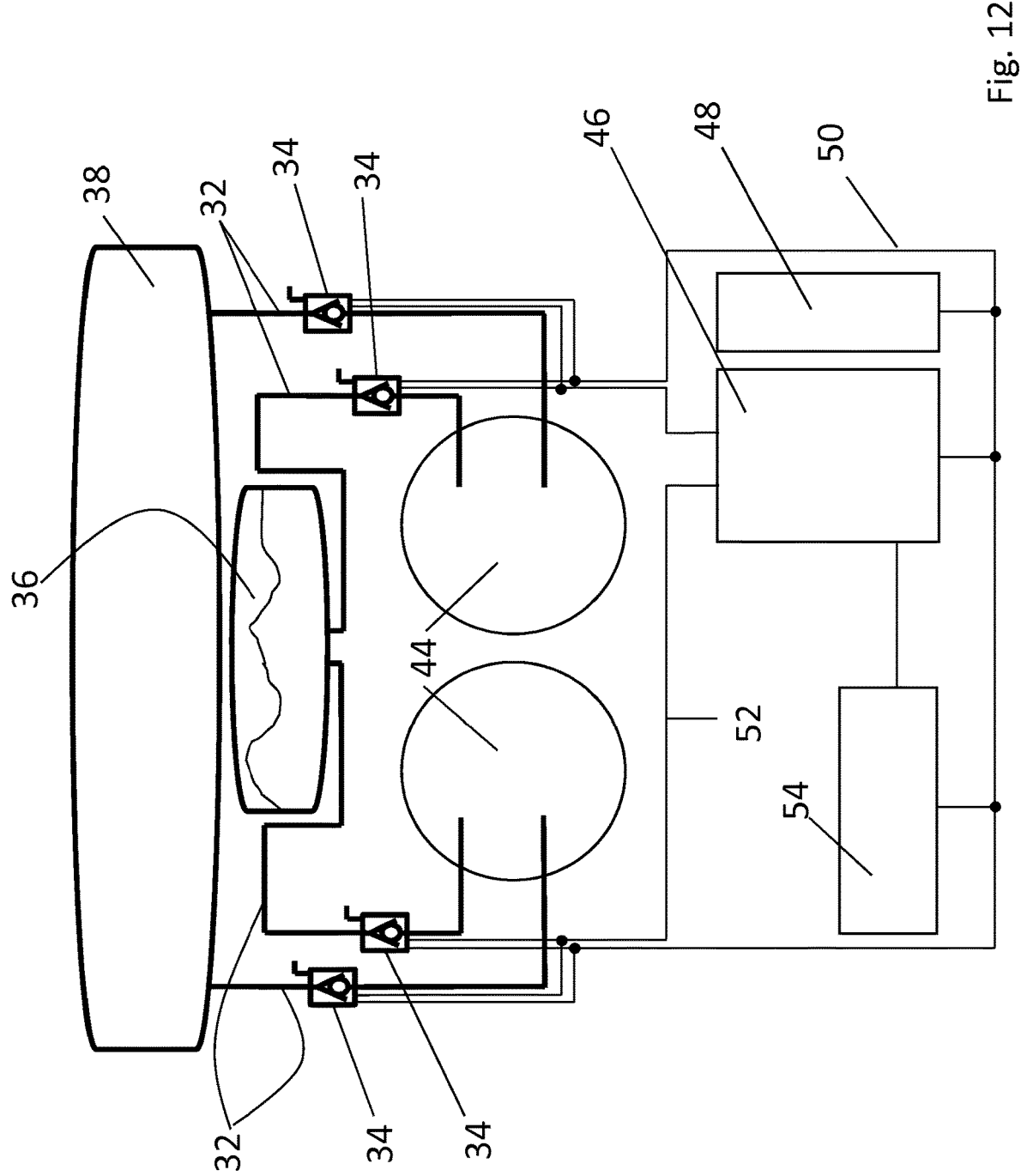

With the exception of those in FIGS. 9, 10 and 12, the embodiments illustrated also feature the second energy store 26. Said energy store may be configured in different way and preferably arranged in such a way that the amount of stored energy increases during a dorsal flexion movement. This energy can be released during a controlled and activated plantar flexion movement. Preferably, this energy store is also a hydraulic or a hydraulic-pneumatic system. Of course, other embodiments of the energy store are also possible.

Figure 11:
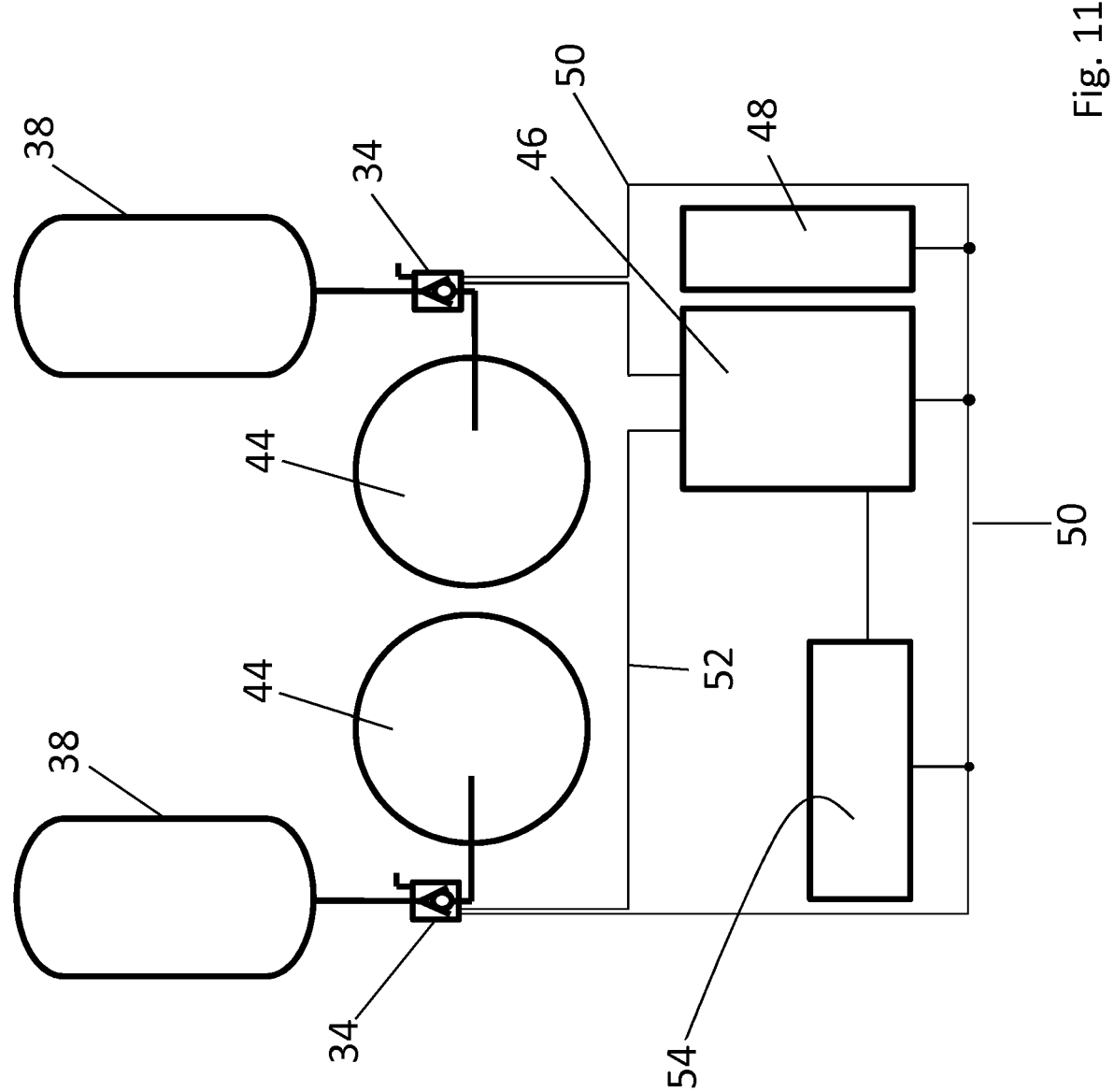

FIG. 11 shows a schematic depiction of a corresponding orthopedic joint device. It comprises two pressure accumulators 38, wherein the left-hand pressure accumulator 38 in FIG. 11 corresponds to the first energy store 8. One rotary hydraulic 44 is allocated to each of the two pressure accumulators 38 to enable energy stemming from the movement of the foot part relative to the lower leg part to be stored. The device has an electronic data processing device 46, which is designed as a microprocessor. A power supply 48 supplies said device with electrical energy. Electrical lines 50 also guide electrical energy to the switchable valves 34.

Said valves are also connected to the electronic data processing device 46 via control lines 52, wherein the valves receive control signals by way of said data processing device. The device also features a sensor system 54, which may feature several different sensors if necessary, the measured values of which are used to control the device.

FIG. 12 shows another configuration. It features a single pressure accumulator 38 and a compensation reservoir 36. The two rotary hydraulics 44 are connected to the pressure accumulator 38 and the compensation reservoir 36 via a fluid line 32. A switchable valve 34 is situated in each of these lines.

The switchable valves are connected to the electronic data processing device 36 via control lines 52 and to the power supply 48 via electrical lines 50. This device also comprises the corresponding sensor system.

Figure 13:
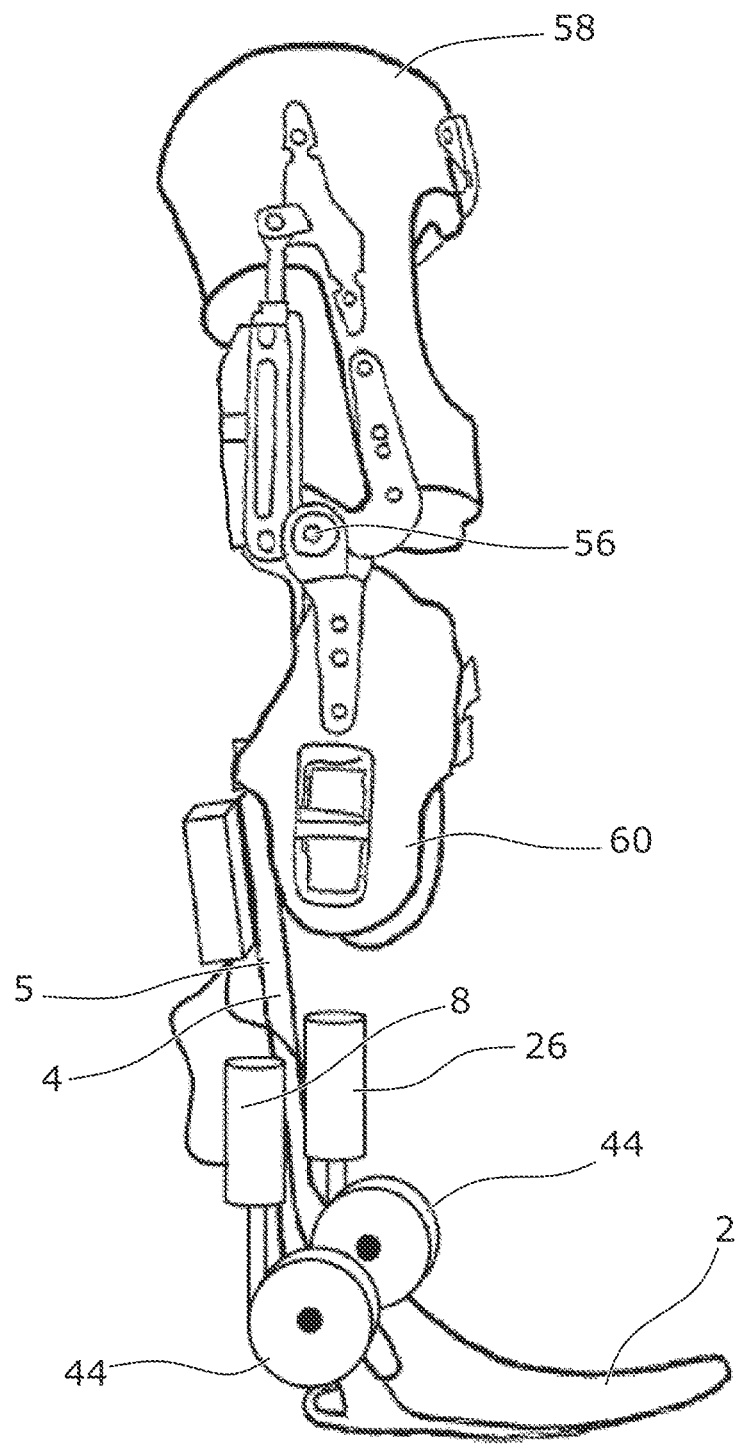

FIG. 13 shows the schematic view of a corresponding orthopedic joint device that is designed as a knee-ankle-foot orthosis. It comprises a foot part 2, the lower leg part 4 as well as a first energy store 8 and a second energy store 26. A joint 56 is located in the knee region. An upper leg shell 58 is situated above said joint and a lower leg shell 60 below for placing it on the upper leg or lower leg. Two rotary hydraulics 44 are provided in the ankle region, one medial and one lateral, said rotary hydraulics being connected to the energy stores 8, 26.

Figure 14:
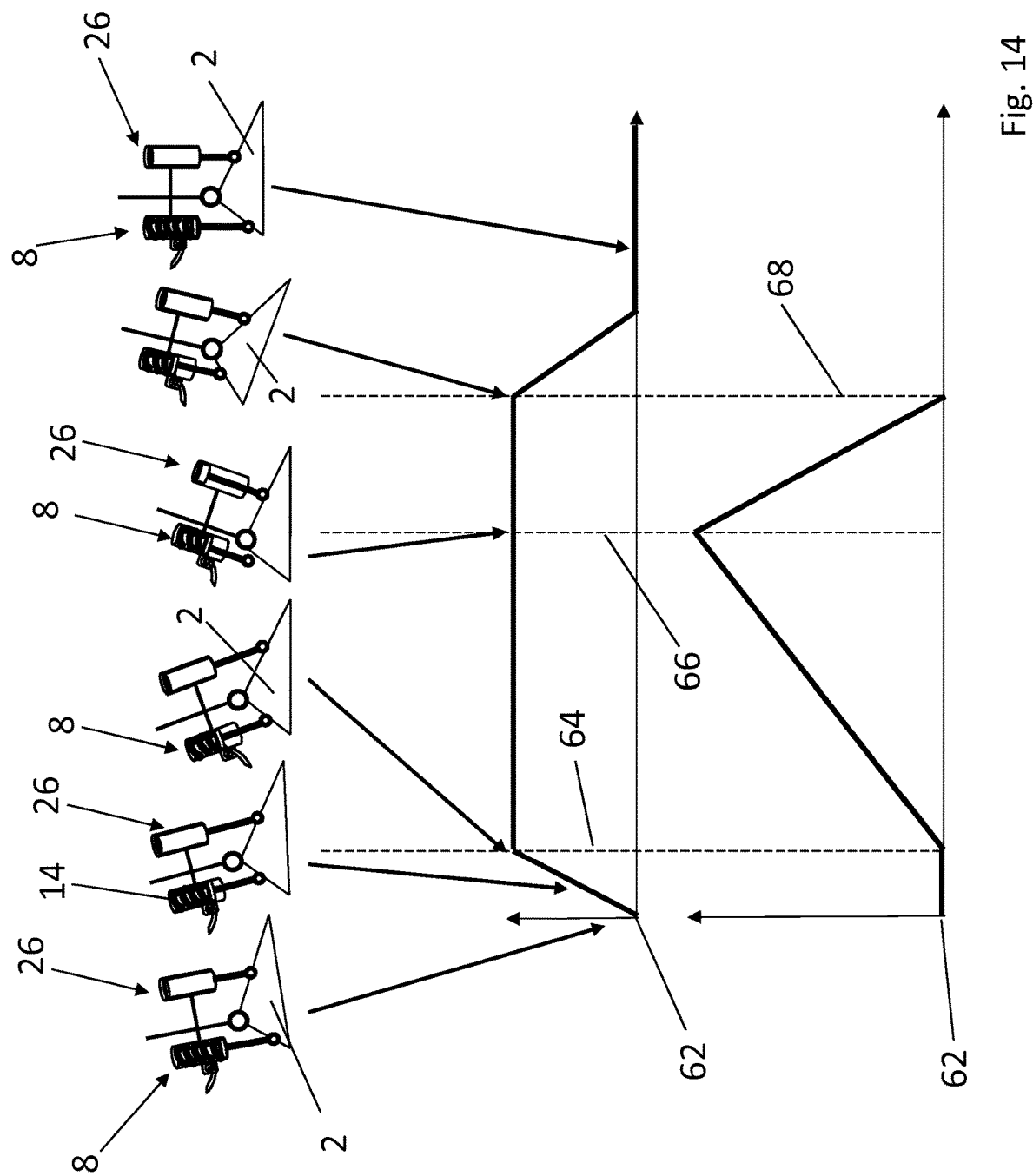

FIG. 14 schematically depicts the progression of the amount of energy stored in the first energy store 8 and in the second energy store 26. In the upper area of FIG. 14, the images from FIG. 2 are shown in a reduced size. The foot part 2 with the first energy store 8 and the second energy store 26 can be seen.

The two diagrams in the lower area schematically depict the amount of energy stored in each store. Here, the upper line indicates the energy stored in the first energy device 8, while the lower line shows the energy stored in the second energy store 26.

Upon the heel strike 62, which is shown by the first image in the first row in FIG. 14, neither the first energy store 8 nor the second energy store 26 contains any energy. This changes with the following controlled plantar flexion, when the energy is stored in the first energy store 8. Said controlled plantar flexion progresses until it reaches the maximum plantar flexion 64, which is depicted by the first dashed line in FIG. 14. In the second image from the left in the first row in FIG. 14, it is clear that the foot part 2 is lowered and the spring 14 in the first energy store 8 is compressed. The third upper image in FIG. 14 shows the maximum plantar flexion position. As described previously in FIG. 2, at this point in time, the release element 22 is brought out of the release position into the locked position. In addition, as shown in FIG. 2, the coupling element 18 is de-coupled from the foot part 2.

Given that the coupling element 18 is de-coupled and the release element 22 is in the locked position, during the following movements, i.e. the controlled dorsal flexion and the active plantar flexion, during which the release element 22 remains in the locked position, the energy level in the first energy store 8 does not change.

The bottom-most diagram in FIG. 14 depicts the amount of energy in the second energy store 26. No energy is stored from the heel strike 62 to the maximum plantar flexion. Energy is stored in the second energy store 26 during the controlled dorsal flexion until the maximum dorsal flexion position 66, wherein said energy is once again released upon the subsequent active plantar flexion and assists with the pushing-off of the foot. This occurs up until the point at which the foot is lifted 68, which is illustrated in the second image from the right in the upper-most line of FIG. 14.

The foot is then in the swing phase, in which, in the example of an embodiment shown, the coupling element 18 has once again coupled the plunger 16 on the foot part 2 and the release element 22 is brought into the release position once again. This enables the energy stored in the first energy store 9 to be released, which causes the foot part 2 to swivel towards the lower leg part 4 about the swivel axis 6. The final position, in which the forefoot region is raised, is shown in the right-hand image of the upper line in FIG. 14. In this state, there is no energy in either the first energy store 8 or the second energy store 26 and the step starts again from the beginning.

FIGS. 15 to 20 show an orthopedic joint device according to a further example of an embodiment of the present invention. The lower leg part 4 is arranged about a swivel axis 6 on the foot part 2 such that it can be swivelled. The first energy store is a spring, which is not depicted. The coupling element 18 is formed by a projection 70, which protrudes from the drawing plane in the selected images, and a driver 72, on which the projection 70 lies in FIG. 15. Given that the projection 70 lies flat on the driver 72, the coupling element 18 is in the coupling position.

In the example of an embodiment shown, the release element 22 is formed by a gearwheel 74 and a ratchet element 76. In the example of an embodiment shown, the ratchet element 76 can be moved upwards and downwards and thus engaged with and disengaged from the gearwheel. This corresponds to the release position when the ratchet element 76 is not engaged with the gearwheel 74 and the locked position when it is engaged.

Figure 15:
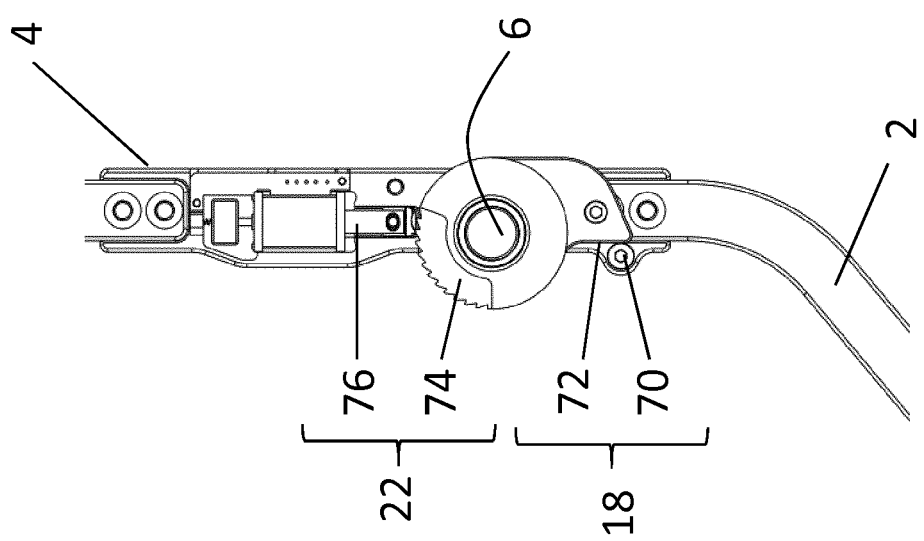

FIG. 15 shows the situation at the start of a step in the maximum plantar flexion position. The complete surface of the foot thus lies on the ground and the foot part 2 is swivelled anti-clockwise to the maximum degree towards the lower leg part 4. The angle between the lower leg part 4 and the foot part 2 is at its maximum. As a result, the projection 70, which is connected to the foot part 2 such that it is torque-proof, has swivelled the driver 72, which is connected to the gearwheel 74 such that it is torque-proof, anti-clockwise relative to the lower leg part 4; in doing so, it has tensioned the spring-not depicted-which represents the first energy store and charged it with energy. The teeth of the gearwheel 74 are designed in such a way that a swivelling of the gearwheel 74 about the swivel axis 6 is possible in this direction, as the ratchet element 76 slides along the slanted teeth of the gearwheel 74.

Figure 17:
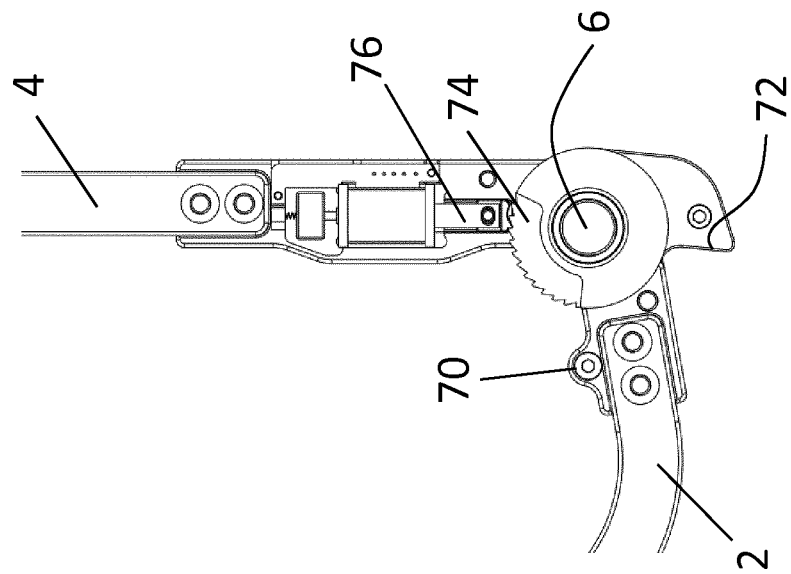
Figure 16:
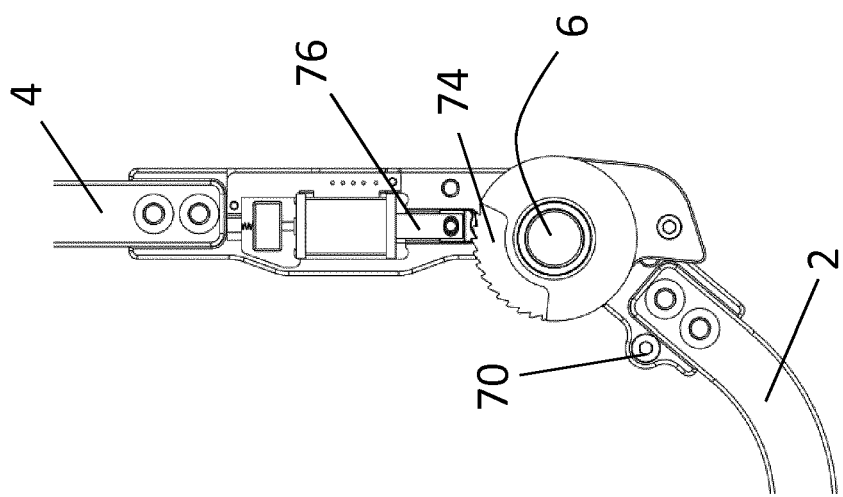

FIGS. 16 and 17 show the middle stance phase (FIG. 16) and the terminal stance phase (FIG. 17). The foot part 2 is swivelled anti-clockwise in relation to the lower leg part 4, thereby effecting a dorsal flexion. The release element 22 remains in the locked position. Both in FIG. 16 and FIG. 17, the ratchet element 76 is engaged with the teeth of the gearwheel 74. This prevent the gearwheel 74 from rotating clockwise about the swivel axis 6, which would discharge the first energy store. Since this is prevented, the release element 22 is in the locked position. Conversely, the coupling element 18 is in the de-coupling position. Neither in FIG. 16 nor in FIG. 17 is the projection 70 in contact with the driver 72, so that the device is in the de-coupling position. In FIG. 17, the joint is in the maximum dorsal flexion position. The angle between the foot part 2 and the lower leg part 4 is at its minimum.

Over the course of the step, a plantar flexion occurs once again when the force is transferred from the foot to the wearer of the orthosis or prosthesis with the joint device in order to push the foot off from the ground towards the next step. This occurs so long as the situation shown in FIG. 18 is reached. It corresponds to the maximum plantar flexion position of the foot part 2 relative to the lower leg part 4 shown in FIG. 15. The coupling element 18 is once again in the coupling position, as the projection 70 lies flat on the driver 72. The release element 22 is still in the locked position, as the ratchet element 76 is still engaged with the gearwheel 74.

In the subsequent swing phase, depicted in FIG. 19, the release element 22 is brought out of the locked position and into the release position. It is clear to see that the ratchet element 76 is moved upwards and is therefore no longer engaged with the gearwheel 74. Said gearwheel is now swivelled clockwise about the swivel axis 6 by way of the mechanical energy stored in the first energy store, which is not depicted. Given that the driver 72 is connected to this gearwheel 74 such that it is torque-proof, it also rotates clockwise about the swivel axis, thereby also moving the close-fitting projection 70 in this direction. As a result of this release of energy by the first energy store, the foot part 2 is swivelled clockwise relative to the lower leg part 4, i.e. in the dorsal flexion direction. This occurs because the coupling element 18 is in the coupling position. At the end of the swing phase, the situation being depicted in FIG. 20, the energy of the first energy store has been completely released and the foot part 2 swivelled relative to the lower leg part 4. To prepare for the next step, which begins with a "heel strike", the release element 22 is brought back into the locked position by moving the ratchet element 76 downwards and causing it to engage once again with the gearwheel 74. The coupling element 18 is still in the coupling position, as the projection 70 lies flat on the driver 72. During the subsequent heel strike and roll-out of the foot, a plantar flexion takes place once again, i.e. an anti-clockwise swivelling of the foot part 2 relative to the lower leg part 4 about the swivel axis 6 in the example of an embodiment shown, until the position shown in FIG. 15 is reached.

We claim:

1. An orthopedic joint device comprising:
   a lower leg part;
   a foot part that is arranged on the lower leg part about a swivel axis such that the foot part is swivelled;
   at least a first energy store;
   a coupling element arranged in a coupling position, in which a swivelling of the foot part relative to the lower leg part about the swivel axis in a plantar flexion direction leads to an increase in the amount of energy stored in the at least a first energy store, and a de-coupling position;
   at least one release element arranged in a release position and a locked position, wherein the energy stored in the at least a first energy store is released by bringing the at least one release element into the release position; and
   an electric control system that is configured to bring the at least one release element out of the locked position and into the release position, and vice-versa.

2. The orthopedic joint device according to claim 1, wherein the energy stored in the at least a first energy store cannot be influenced by the swivelling of the foot part relative to the lower leg part when the coupling element is in the de-coupling position.

3. The orthopedic joint device according to claim 1, further comprising at least one pressure, position, force or acceleration sensor, which is configured to record at least one measured value and to transmit the at least one measured value to the electric control system.

4. The orthopedic joint device according to claim 3, wherein the electric control system is configured to bring the at least one release element out of the locked position into the release position, depending on the at least one transmitted measure value.

5. The orthopedic joint device according to claim 3, wherein the electric control system is configured to detect a loss of ground contact of the orthopedic joint device using the at least one transmitted measured value, and to bring the at least one release element out of the locked position into the release position when the loss of ground contact has been detected.

6. The orthopedic joint device according to claim 1, wherein the electric control system is configured only to bring the coupling element from the coupling position into the de-coupling position when the at least one release element is in the locked position.

7. The orthopedic joint device according to claim 1, further comprising a second energy store, which is configured in such a way that the swivelling of the foot part relative to the lower leg part about the swivel axis in a dorsal flexion direction leads to an increase in the amount of energy stored in the second energy store.

8. The orthopedic joint device according to claim 7, wherein the at least a first energy store or the second energy store include a spring element or a hydraulic device or a pneumatic device.

9. The orthopedic joint device according to claim 8, wherein two rotary hydraulics are allocated to the joint device.

10. The orthopedic joint device according to claim 1, wherein the coupling element is designed as a fluid-valve combination.

11. An orthopedic joint device comprising:
a lower leg part;
a foot part that is pivotally mounted to the lower leg part about a rotation axis;
at least one energy store;
a coupling element arranged in a coupling position, in which a pivoting of the foot part relative to the lower leg part about the rotation axis in a plantar flexion direction leads to an increase in the amount of energy stored in the at least one energy store, and a de-coupling position;
at least one release element movable between a release position and a locked position, wherein the energy stored in the at least one energy store is released by bringing the at least one release element into the release position; and
an electric control system that is configured to bring the at least one release element out of the locked position and into the release position, and vice-versa.

12. The orthopedic joint device according to claim 11, wherein the energy stored in the at least one energy store is independent of the pivoting of the foot part relative to the lower leg part when the coupling element is in the de-coupling position.

13. The orthopedic joint device according to claim 11, further comprising at least one sensor, the at least one sensor including a pressure, position, force or acceleration sensor, the at least one sensor is configured to record at least one measured value and to transmit the at least one measured value to the electric control system.

14. The orthopedic joint device according to claim 13, wherein the electric control system is configured to bring the at least one release element out of the locked position into the release position, depending on the at least one transmitted measure value.

15. The orthopedic joint device according to claim 13, wherein the electric control system is configured to detect a loss of ground contact of the orthopedic joint device using the at least one transmitted measured value, and to bring the at least one release element out of the locked position into the release position when the loss of ground contact has been detected.

16. The orthopedic joint device according to claim 11, wherein the electric control system is configured to bring the coupling element from the coupling position into the de-coupling position when the at least one release element is in the locked position.

17. The orthopedic joint device according to claim 11, further comprising a second energy store, which is configured in such a way that the pivoting of the foot part relative to the lower leg part about the rotation axis in a dorsal flexion direction leads to an increase in the amount of energy stored in the second energy store.

18. The orthopedic joint device according to claim 11, wherein the at least one energy store includes a spring element or a hydraulic device or a pneumatic device.

* * * * *